Sept. 16, 1975 J. C. MIKKELSEN Plant Pat. 3,781
BEGONIA PLANT
Filed Aug. 19, 1974
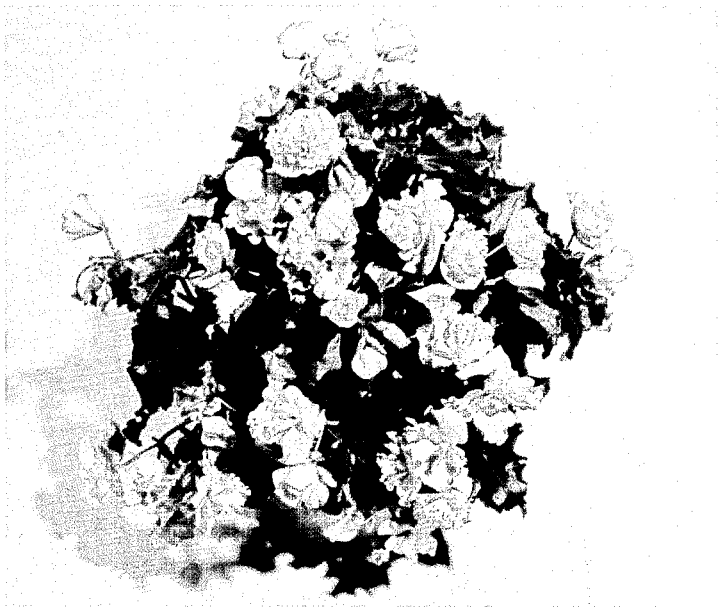

United States Patent Office

Plant Pat. 3,781
Patented Sept. 16, 1975

3,781
BEGONIA PLANT

James C. Mikkelsen, Ashtabula, Ohio, assignor to
Mikkelsens Inc., Ashtabula, Ohio Filed Aug. 19, 1974, Ser. No. 498,865
Int. Cl. A01h *5/00*
U.S. Cl. Plt.—68 1 Claim The present invention relates to a new and distinctive variety of begonia plant, known by the varietal name Aphrodite Twinkles and botanically known as *Begonia elatior* (B × *hiemalis*—Fotsch), discovered by me as a mutation in the form of a axillary shoot in a crop of flowering plants of the parent, unpatented cultivar Aphrodite Rose. Asexual reproduction initially by stem cuttings has reproduced the unique features of the variety through successive propagations. Subsequent research has demonstrated over numerous propagation experiments that leaf cuttings of this new variety also propagate extremely well.

The following characteristics distinguish the new begonia from both its parent and other begonias commercially known and used in the floriculture industry:

1. Very small foliage with sharp serrations. Will become chlorotic if pH is above 6.
2. Very short, compact growth—a definite dwarf type compared to the presently existing Rieger Aphrodite begonias.
3. Prolific self-branching allowing for a very full plant, a valuable asset for stem cutting propagation.
4. Small semi-double azalea type flowers—tends to have a continuous profusion of flowers. Flowers considered long lasting.
5. Flowers are ruffled and light rose in color.
6. The new variety can be easily grown as an upright plant with minimal staking.
7. The prolific self-branching characteristic of the new cultivar permits advantageous use of the new cultivar for hanging baskets.
8. By manipulating the growing time in accordance with greenhouse culture, the variety is versatile for "mini-plant" for the home, or large specimen display plants.
9. The most outstanding feature is that this new variety can be propagated by leaf cuttings allowing the grower to receive multiple shooted vegetative plants as in the Schwabenland begonia types.

The above noted distinguishing characteristics of the new cultivar result in the new cultivar being one of the most versatile begonias developed to date.

The accompanying colored photographic drawing illustrates the overall appearance of the new variety, with the color being as true as reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

*Parentage:* Mutation from unpatented cultivar Aphrodite Rose.

*Propagation:* By stem cuttings in four weeks. Rapid and profuse self-branching produces a large volume of cuttings in small area. Small cuttings can be propagated very close together. Leaf cuttings with six to eight adventitious shoots can be shipped in eight weeks after beginning of propagation.

*Rooting Habits:* Very rapid, fine dentritic root system.

*Plant Form:* Very bushy.

*Habit of Growth:* Definitely upright; profusion of secondary growth causes soft growth and toppling of side shoots.

*Blooming Habits:* After flower initiation, blooming is continuous over a very long period of time; up to 6 to 8 months.

*Blooming Season:* Normally early November. Leaf propagation allows for development of vegetative plants for precise control of flowering with proper greenhouse techniques.

*Foliage:* Oval, small, dark green, sharp serration; over abundant due to self-branching characteristic of the new cultivar.

- *Size*—Four to six cm. in diameter.
- *Shape*—Oval to round; transitional from young to old leaves.
- *Texture*—Smooth, firm.
- *Margin*—Strongly serrated on young foliage.
- *Color*—New: top, color 137A; under, color 147C, yellow green. Old: top, color darker than 139A; under, color 147B with red infusion.

*Disease Resistance:* Seems quite resistant to mildew compared to other begonias—mildew infections not seen to date.

*Flowers:*

- *Borne*—On trusses flowering alternately and continuously over 6 to 8 months.
- *Quantity*—Extremely high because of the great number of growing points associated with the characteristic of self-branching.
- *Buds*—Flat, small 5 to 10 mm. in diameter; open flowers are 4 cm. in diameter.
- *Tepals*—Have ruffled edges, color red 52A.
- *Reproductive Organs:* Stamens—None seen to date. Pollen—None seen to date. Styles/ovaries—None seen to date.

I claim:

1. A new and distinct cultivar of begonia characterized particularly as to uniqueness by its prolific self-branching habit allowing for a very full plant; short, compact growth giving a dwarf type appearance; its ability to be easily propagated by leaf as well as stem cuttings; small semi-double azalea type flowers which bloom continuously for up to six to eight months; very small foliage with sharp serrations, and by its superior versatility which permits the cultivar to be grown either as a small plant for the home or as a large plant for display.

No references cited.

ROBERT E. BAGWILL, Primary Examiner